United States Patent [19]
Gray

[11] Patent Number: 5,967,772
[45] Date of Patent: Oct. 19, 1999

[54] ORTHODONTIC ANCHOR SYSTEM

[76] Inventor: James B. Gray, 715 Shade Tree Ter., Roswell, Ga. 30075

[21] Appl. No.: 09/208,158

[22] Filed: Dec. 9, 1998

[51] Int. Cl.$^6$ ........................................... A61C 3/00
[52] U.S. Cl. ................................. 433/7; 433/18; 433/21; 433/24
[58] Field of Search ................................. 433/7, 18, 21, 433/24

[56] References Cited

U.S. PATENT DOCUMENTS

| | | | |
|---|---|---|---|
| Re. 23,511 | 6/1952 | Noyes | 433/169 |
| Re. 35,170 | 3/1996 | Arndt et al. | 433/7 |
| 1,582,570 | 4/1926 | Brust | 433/7 |
| 2,571,931 | 10/1951 | Noyes | 433/169 |
| 3,162,948 | 12/1964 | Gerber | 433/7 |
| 3,284,902 | 11/1966 | Dillberg et al. | 433/7 |
| 3,792,529 | 2/1974 | Goshgarian | 433/7 |
| 4,026,023 | 5/1977 | Fisher | 433/7 |
| 4,028,808 | 6/1977 | Schwartz | 433/7 |
| 4,045,871 | 9/1977 | Nelson | 433/7 |
| 4,239,487 | 12/1980 | Murdock | 433/7 |
| 4,373,913 | 2/1983 | McAndrew | 433/7 |
| 4,408,989 | 10/1983 | Cleary | 433/7 |
| 4,468,196 | 8/1984 | Keller | 433/24 |
| 4,571,178 | 2/1986 | Rosenberg | 433/18 |
| 4,573,914 | 3/1986 | Nord | 433/18 |
| 4,592,725 | 6/1986 | Goshgarian | 433/7 |
| 4,723,910 | 2/1988 | Keller | 433/7 |
| 4,815,968 | 3/1989 | Keller | 433/7 |
| 4,854,864 | 8/1989 | Cleary | 433/7 |
| 5,007,828 | 4/1991 | Rosenberg | 433/18 |
| 5,066,224 | 11/1991 | Block et al. | 433/7 |
| 5,074,784 | 12/1991 | Serrett et al. | 433/18 |
| 5,167,499 | 12/1992 | Arndt et al. | 433/7 |
| 5,167,500 | 12/1992 | Miura | 433/7 |
| 5,205,736 | 4/1993 | Blechman | 433/18 |
| 5,312,247 | 5/1994 | Sachdeva et al. | 433/7 |
| 5,334,015 | 8/1994 | Blechman | 433/18 |
| 5,399,087 | 3/1995 | Arndt | 433/7 |
| 5,505,616 | 4/1996 | Harwell | 433/21 |
| 5,538,427 | 7/1996 | Hoffman et al. | 433/173 |
| 5,645,422 | 7/1997 | Williams | 433/7 |
| 5,697,779 | 12/1997 | Sachdeva et al. | 433/2 |
| 5,785,520 | 7/1998 | Carano et al. | 433/7 |
| 5,836,768 | 11/1998 | Huskens et al. | 433/24 |
| 5,885,290 | 3/1999 | Guerrero et al. | 433/7 |

*Primary Examiner*—John J. Wilson
*Attorney, Agent, or Firm*—Womble Carlyle Sandridge & Rice

[57] ABSTRACT

The present invention is an orthodontic anchor system for controlling or altering the position of teeth, which is comprised of an anchor for selective attachment to a palate, a transpalatal member having a first and second end, where either the first end is attached to the anchor and the second end is attached to a tooth or teeth, or the first and second end are each respectively attached to a tooth or teeth and a center portion of the transpalatal member is attached to the anchor, and a stress breaker that is included either within the transpalatal member or between the anchor and transpalatal member. The anchor can be comprised of one or more dental implants or subperiosteal implants with the transpalatal member either attached directly thereto, or the stress breaker is directly attached thereto and also attached to the transpalatal member. The stress breaker is preferably comprised of a biasing element or a spring. The system alternatively includes one or more bands which slidably secure about a tooth and to which an end of the transpalatal member selectively attaches.

22 Claims, 5 Drawing Sheets

ORTHODONTIC ANCHOR SYSTEM

FIELD OF THE INVENTION

The present invention generally relates to the field of orthodontic appliances. More particularly, the present invention relates to an orthodontic anchor system for securing orthodontic appliances or devices for controlling or altering the position of a desired tooth or teeth.

DESCRIPTION OF THE RELATED ART

Orthodontic appliances are widely used for positioning and adjusting teeth to optimize the formation of the maxillary and mandibular dental arches. The specific positioning of and the forces applied by the appliances varies according to the desired position of the teeth. Two common types of orthodontic appliances used include orthodontic wires and "braces," and transpalatal arch bars.

Orthodontic wires are generally secured through a plurality of braces, each affixed to a tooth whereby the positioning of teeth relative to each other can be controlled and adjusted. The adjustment of the position of teeth is accomplished by providing forces in the desired direction. For many desired forces, there are unwanted reciprocal forces that often limit the direction, amount, and efficiency of orthodontic tooth movement.

The attempt to control these unwanted forces is called anchorage. All intraorally derived anchorage tends to be unstable and not completely predictable due to the many factors influencing the teeth. These include, $inter\ alia$, the forces of occlusion (which is the force generated through mastication or biting or chewing of food), the differential size of teeth, the density of the bone through which the teeth are being removed, and the friction of the braces. Many extensive procedures such as the extraction of teeth, the use of headgears, cumbersome intraoral devices, and surgery on the jaw to move sections of teeth (orthognathic surgery) are necessary in orthodontic treatment as compensation for the unwanted reciprocal forces.

Furthermore, while the usage of bulky headgears provides relatively stable anchorage, successful adjustment is heavily dependent on the patient's utmost cooperation. Thus, it has typically been necessary to use bulky or cumbersome headgear together with the orthodontic wires to try to hold the wires in position. Such headgear, however, can shift or otherwise be easily dislodged and must be specially fit and adjusted to each patient.

Attempts have been made to try to further secure such orthodontic wires using orthodontic implants that are directly attached to the palatal bone. Attempts have been made to try to control anchorage using intraoral subperiosteal, or "onplant," devices that are adhered on the palatal bone. Examples of on-plant devices are disclosed in U.S. Pat. Nos. 5,538,427 and 5,066,224. In general, these anchors are installed by making an incision into the patient's mouth in the soft tissue at a palatal site to create a flap. The flap is peeled back, the anchor attached to the palatal bone, and the flap reapplied about the anchor. After sufficient healing, the anchor is surgically exposed and the orthodontic wires are then attached to the anchors, substantially eliminating the need for bulky headgear.

The forces of occlusion acting upon the wires and the anchors necessitates the anchors to be of a sufficient size to have sufficient strength to withstand the forces of occlusion without failure. Such size constraints further require deeper and/or more extensive attachment to the palate of the patient to avoid their being pulled free when subjected to forces of occlusion. The surgical procedures for installing anchors are highly invasive and often quite painful to the patient. Also, these surgical procedures are expensive and typically require significant healing time and an additional procedure is needed to remove these anchors at the completion of the procedure.

Also, to anchor or position a tooth or teeth, it is common to use a transpalatal arch bar to help manipulate a specific tooth or teeth. The arch bar can be formed with a variety of shapes or configurations and typically is formed from a metal or alloy material having a shape memory for applying expansion, rotational, intruding or torque forces to desired teeth, and typically is connected to teeth on opposite sides of a patient's mouth, spanning the palatal area of the patient's mouth. Examples of such transpalatal arch bars are shown in U.S. Pat. Nos. 3,792,529; 4,408,989; 4,592,725; 4,815,968; 4,854,864; 5,312,247; and 5,167,499. These references illustrate various embodiments of transpalatal arch bars which rigidly or semi-rigidly attach to a plurality of teeth, typically within the maxillary dental arch. Several of these transpalatal arch bars, such as U.S. Pat. No. 4,408,989 to $Cleary$, include U-shaped projections, loops, or other shapes formed into the arch bar to provide a flexibly biased rigidity to the arch bar to maintain the position of the patient's teeth to which the bar is attached. U.S. Pat. No. 5,312,247 further discloses constructing the transpalatal arch bar out of a superelastic alloy to enhance the supply of a substantially constant corrective force to the teeth.

As with orthodontic wires, transpalatal arch bars generally are subjected to forces of occlusion. To accordingly minimize the effect of occlusive forces on the effectiveness of dental appliances, appliances have been developed with stress breakers to absorb the occlusive forces. An example of a dental appliance including a general stress breaker is U.S. Pat. No. Re. 23,511.

Thus, there exists a need for an orthodontic system to position and adjust a tooth or teeth of a patient that is able to withstand occlusive or other reciprocal forces applied thereto, and which is less expensive and time consuming to install, and is less invasive to the patient than conventional anchor systems. It is to the provision of such an improved orthodontic anchor system that the present invention is primarily directed.

SUMMARY OF THE INVENTION

Briefly described, the present invention generally comprises an orthodontic anchor system for supporting an orthodontic appliance or device for positioning or adjusting a tooth or teeth of a patient. The orthodontic anchor system includes an anchor selectively attached to the palate of the patient and a transpalatal member that is attached to the anchor and is selectively attached to at least on tooth. Generally, the anchor comprises one or more endosseous implants or subperiosteal onplants that are attached or to the palatal bone. For example, with use of dental implants of the type that include a threaded shank and a head having a cap mounted thereon, a local anesthesia is applied to the tissue at the implant site and the implant generally is drilled or inserted into the palatal bone. For on-plant type devices, after a local anesthesia has been applied, a small incision is made in the soft tissue over the palatal bone and the on-plant device is allowed to heal to the bone using material, such as a hydroxyapatite or bioactive glass.

The implants or on-plant devices used for the anchor are of a significantly reduced size so as to make their installation considerably less invasive and as to significantly reduce the trauma to the patient so that these implants or on-plants can be inserted into or applied to the palatal bone of the patient generally in a single office visit on an out-patient basis. The head portions of the implants further generally are exposed within the mouth and can include caps that fit over and are secured to the head portions or the head portions themselves. Such caps typically have recesses or attachment slots formed therein for connection of the anchor to either the transpalatal member or to a stress breaker.

The transpalatal member generally is a palatal arch bar formed from a metal or alloy material having superelastic and shape memory properties or characteristics. The transpalatal member also can be formed in a variety of shapes or configurations as needed for imparting a force to a tooth or series of teeth in the patient's mouth. For transpalatal members used with implants as the anchor mechanism, the transpalatal member typically will have opposite first and second ends that are attached to one or more teeth of the patient by tubes or ligatures and an intermediate or center portion that extends through and attaches to a stress breaker. For use with on-plant type devices as an anchor, the transpalatal member generally will have at least a first end attached to the anchor and a second or a distal end that attaches to at least one tooth, with a stress breaker formed along an intermediate portion between the proximal and distal ends of the transpalatal member. It is also possible to attach the transpalatal member to the on-plant and the patient's teeth in a fashion similar to use with implants, and to use additional or multiple stress breakers between the ends of the transpalatal members as necessary or desired.

Typically, the stress breakers will include a center sleeve or connecting member through which the transpalatal member is received and one or more shock absorbing members, such as torsional or leaf springs or coil springs, that are attached to the center connector along one side thereof and connected to the anchor mechanism. The use of the stress breakers in conjunction with the anchor mechanisms for connecting to and supporting the transpalatal member enables the anchors to better withstand the forces of occlusion transmitted by the transpalatal member during chewing or other engagement of the teeth of the patient. As a result, the anchor mechanisms used are of a significantly reduced size, which are thus less invasive and cause significantly less trauma to the patient during installation. Thus, the installation procedure can be accomplished typically using a local anesthesia as an in-office/out-patient procedure with a minimum of discomfort and time and expense required to complete the procedure to provide an orthodontic anchor system for the positioning and adjustment of a tooth or teeth of a patient and which provides consistent and substantially precise application and position forces with the amount of adjustment of the system that is required being minimized.

Additionally, the design of the stress breaker imparts not only the ability to protect the anchor or on-plants from destructive occlusal forces but, through flexibility, also allows adjustment of the device to provide corrective orthodontic forces. By adjusting the transpalatal bar, the flexibility of the stress breaker will provide directional forces for orthodontic tooth movement while reducing unwanted reciprocal forces. Importantly, the design of the appliance also facilitates easy removal and placement of the transpalatal member for the anchor to allow adjustment as needed throughout orthodontic treatment.

Various objects, features and advantages of the present invention will become apparent to those skilled in the art upon review of the following detailed description of preferred embodiments, when taken in conjunction with the accompanying drawings.

DETAILED DESCRIPTION OF PREFERRED EMBODIMENTS

Figure 1:
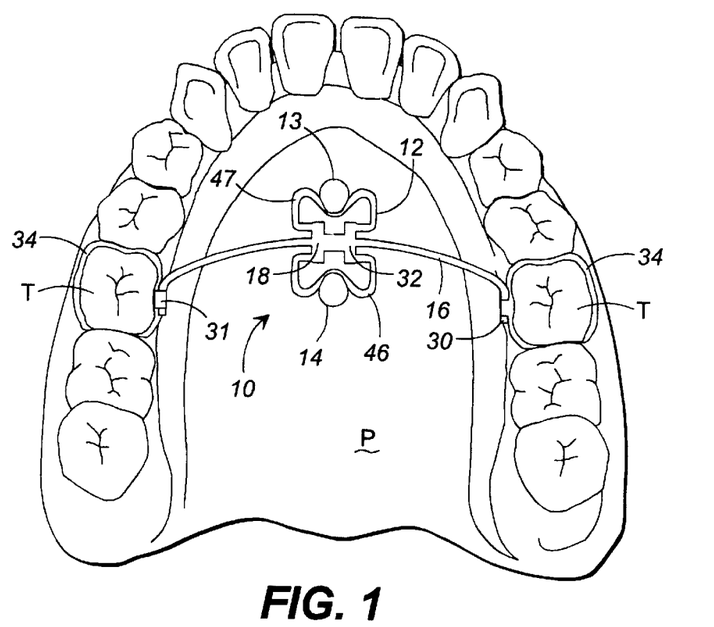
FIG. 1 is a bottom view of a first embodiment of the orthodontic anchor system, illustrating the anchors and a transpalatal member with a stress breaker therebetween.

Referring now in greater detail to the drawings, in which like numerals represent like components throughout the several views, FIG. 1 illustrates a first preferred embodiment of the orthodontic anchor system 10 of the present invention for securing an orthodontic appliance or devices within the mouth of a patient for use in applying adjusting forces to the patient's teeth. The anchor system 10 includes an anchor mechanism 12, shown in the present embodiment as including a plurality of dental implants 13 and 14, a transpalatal member 16, and a stress breaker 18. The implants 13 and 14 of the anchor mechanism 12 of this first embodiment are minimized in size so as to be unobtrusive of eating and to likewise minimize the trauma to the tongue and palate of the patient during insertion of the implants and thereafter while the orthodontic appliance is worn by the patient. Accordingly, the implants typically will be approximately 14 to 21 mm in length with approximately 3 to 6 mm of the implant being exposed from the palate when secured in the patient's mouth. However, as further described below, it is possible to use anchors of other, varying dimensions and types, including subperiosteal and other types of conventional anchors. Therefore, while the present implants are being disclosed with reference to a preferred range of sizes, such a preferred range is for illustrative purposes only and it will be understood by those skilled in the art that various other types of conventional dental implants and varying sizes of greater than 16 to 18 mm also may be used.

Figure 2:
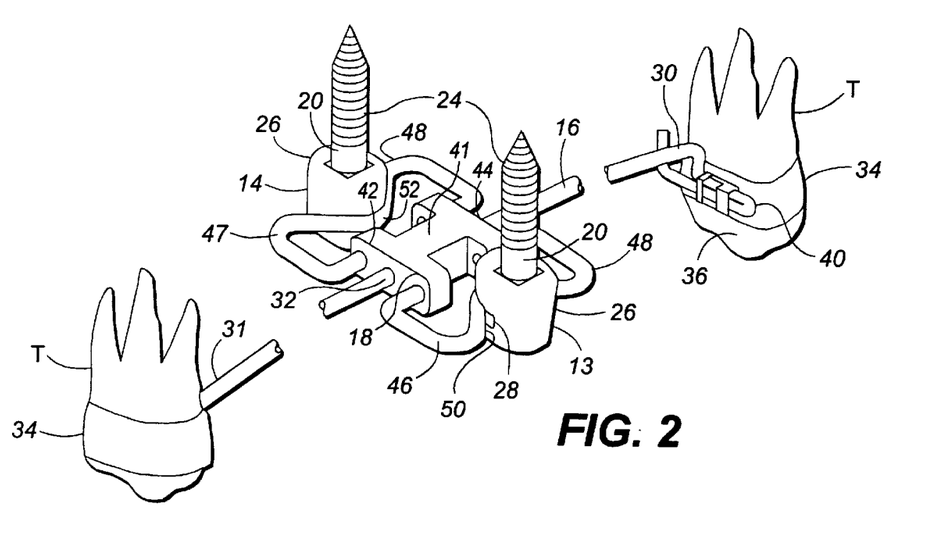
FIG. 2 is a cut-away perspective view of the orthodontic anchor system of FIG. 1.
Figure 3:
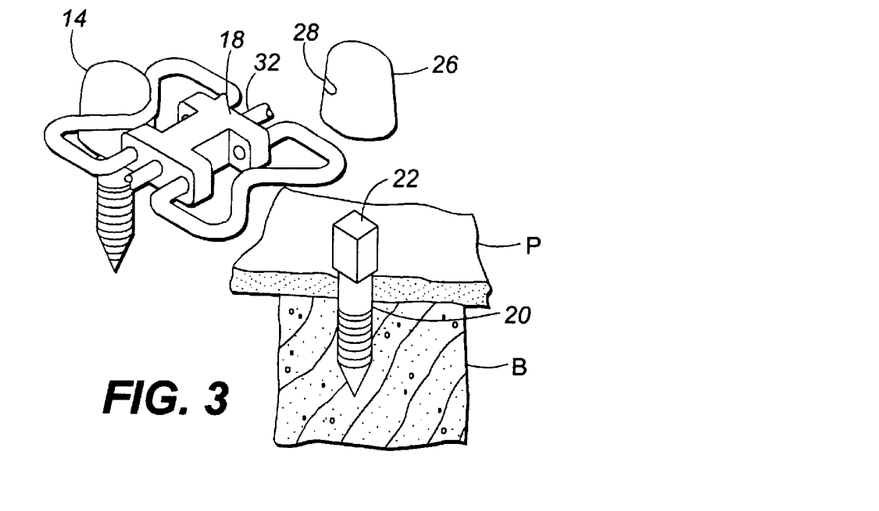
FIG. 3 is a perspective view of the anchors and stress breaker of the orthodontic anchor system of FIG. 1, illustrating one of the anchors affixed within the palate of a patient.

FIGS. 2 and 3 illustrate implants 13 and 14 in further detail. As shown, each implant typically includes a shank 20 that is inserted or drilled into the palate "P" of the mouth of the patient so as to be embedded into the palatal bone, and a head or upper portion 22 (FIG. 3) exposed from the palate. The shank portions 20 of the implants illustrated in FIGS. 2 and 3 further typically include threads 24 to enable the implants to be drilled into the palate, although it will be understood by those skilled in the art that the implants also can have substantially smooth sided shanks. Each implant further generally includes a cap 26 (FIG. 3) that is received over and covers the head 22 of each implant and which further includes a recess or attachment slot 28 formed in one side thereof. Additionally, each dental implant or subperiosteal implant, as discussed below, alternatively can be coated with a hydroxylapatite to facilitate the attachment of the tissues and bones to the surface of the dental implant. It should be noted that the use of a hydroxylapatite or other bioreactive coating or bonding mechanism is not required and that such use with the implant further can affect the removability of the implant from the palate of the patient when the orthodontic anchor system no longer is desired, but may be used under conditions where necessary or desired to strengthen the attachment of the implant to the palate of the patient. It further is possible to use additional implants or possibly a single implant depending on the requirements of the orthodontic appliance to be supported by the implants.

As illustrated in FIGS. 1 and 2, the transpalatal member 16 generally is a conventional transpalatal or arch bar as is known in the art and which is formed from a metal such as stainless steel, a nickel titanium alloy, titanium molybdenum alloy, or other type of superelastic alloy or potentially a ceramic or plastic material, having superelastic strength and shape memory characteristics. In the embodiment shown in FIGS. 1 and 2, the transpalatal member is illustrated as having a substantially arched or C-shape, but it will be understood that other shapes or configurations such as an M or W-shaped bar or an arched bar having loops, indentations, or projections formed therein also can be used. The transpalatal member includes a first end 30, second end 31, and a center or intermediate portion 32. The ends 30 and 31 of the transpalatal member are attached to selected teeth of the patient with the transpalatal member being bent or arched between the teeth so as to provide a biasing, contracting, rotational or other adjustment force to the teeth for adjusting the position of the teeth. As shown in FIG. 2, bands 34 attached or encircled about the desired teeth to be positioned or adjusted. Such orthodontic bands generally are made from a metal material such as a stainless steel or other material that is resistant to corrosion and moisture, and typically have a sleeve or tube 36 formed therealong and in which one end of the transpalatal member is received and secured to thus attach the transpalatal member to the tooth of the patient. It will further be recognized by those skilled in the art that other types of attachment mechanisms for attaching the transpalatal member to a desired tooth or teeth can be used in place of the bands or ligatures 34, including direct attachment mechanisms as are known in the art.

As illustrated in FIGS. 1 and 2, the stress breaker 18 is positioned between the implants of and connected to the torsional springs of the anchor mechanism 12, mounted to the transpalatal member 16 along its intermediate or center portion 32. The stress breaker 18 generally includes a central connector which can comprise a square block, cylindrical tube or, as shown in the first embodiment of FIGS. 1–3, other shape such as a substantially I-shaped block, typically formed from a metal such as stainless steel, nickel titanium alloy or other type of rigid, noncorrosive material, including the same type of material as used for the transpalatal bar. The connection has a central portion 41 through which the intermediate portion 32 of the transpalatal member 16 is received and extends, and transversely extending end portions 42 and 44. Biasing elements 46 and 47 are attached to transverse ends 42 and 44 of the center connector of the stress breaker 18 and are further received and held within the recesses or attachment slots 28 of the caps 26 of the implants 13 and 14 as illustrated in FIG. 2. Typically, the biasing elements will be springs, here illustrated as torsional or leaf springs, and can also include tension springs such as coil springs or a section of spring steel or other elastic members.

Figure 4A:
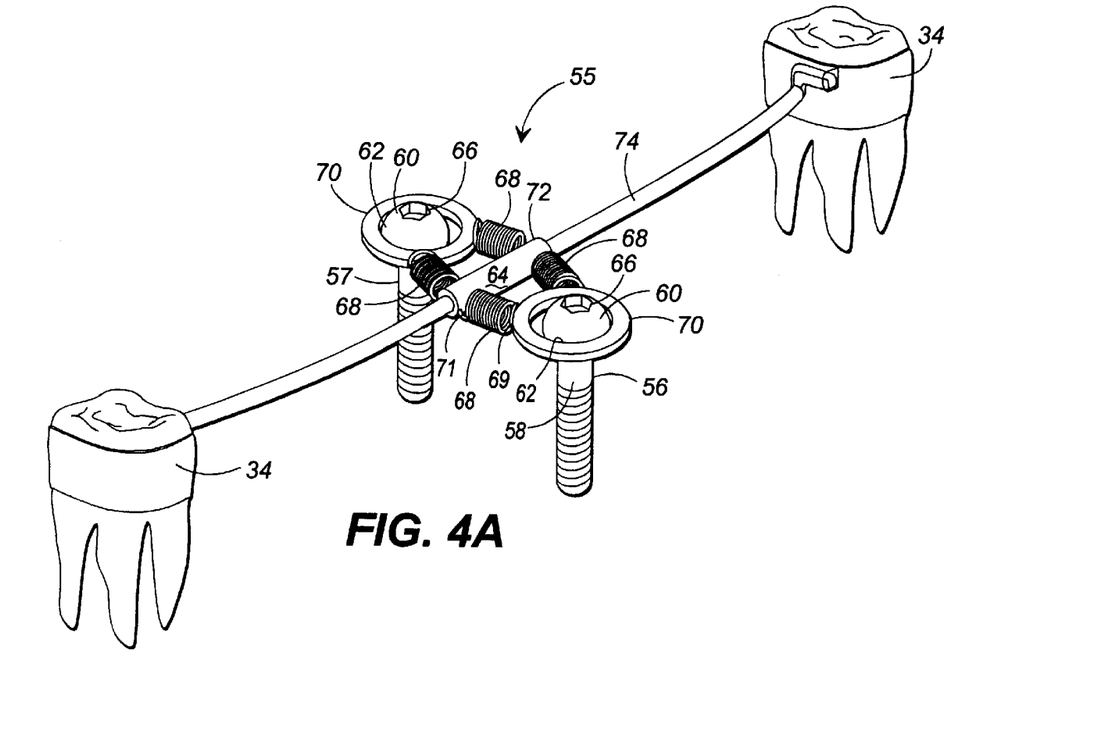
FIG. 4A illustrates an alternate embodiment of the orthodontic anchor system, wherein the stress breaker is comprised of a plurality of springs connected between the transpalatal member and anchors.
Figure 4B:
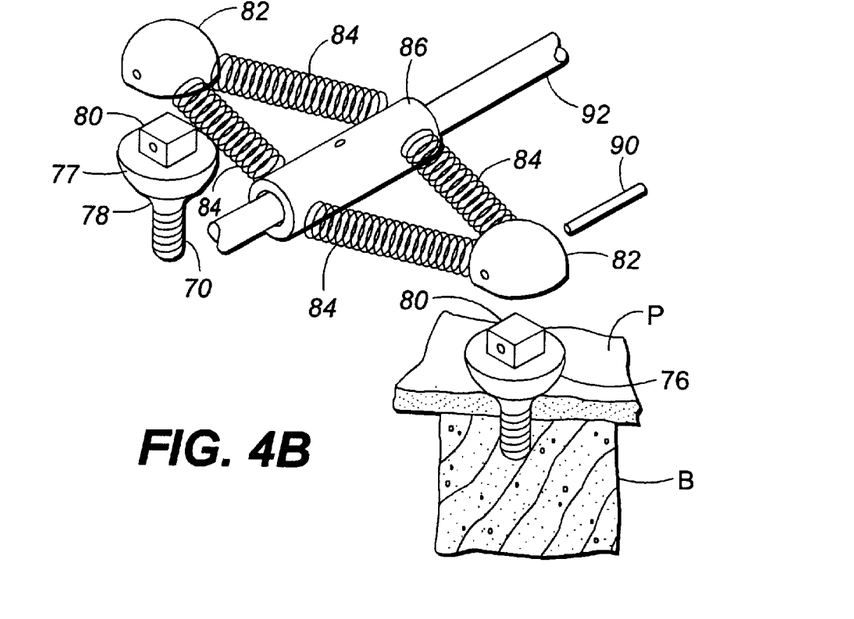
FIG. 4B is an exploded perspective view of another alternate embodiment of the orthodontic anchor system similar to FIG. 4A and further illustrating one of the anchors affixed within the palate.
Figure 7:
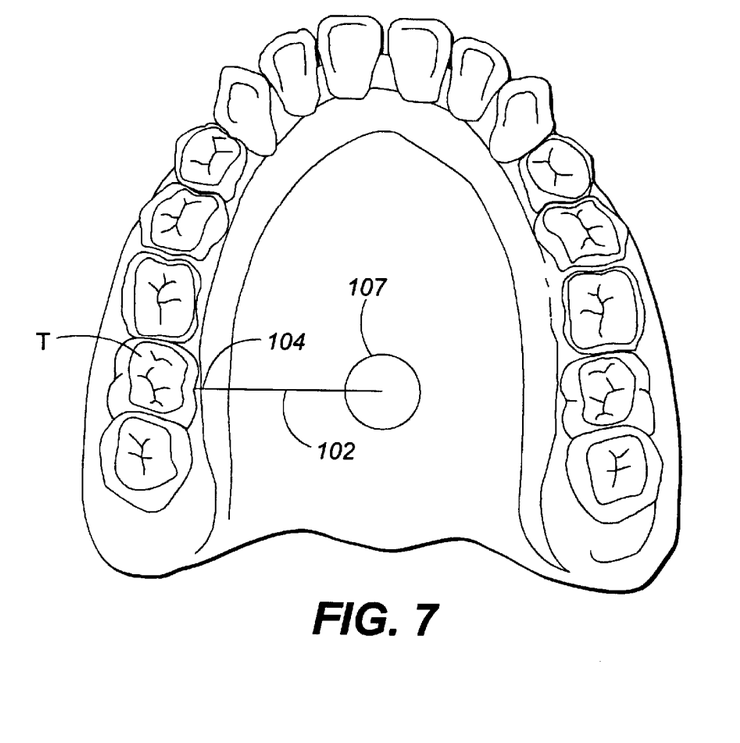
FIG. 7 is a bottom view of the orthodontic anchor system in FIG. 6 affixed to the palate in a patient's mouth.

The stress breaker tends to impart a biasing force to stabilize the transpalatal member and is thus disclosed herein as a semi-rigid metal biasing element, shown in FIGS. 1–3, plurality of springs, as shown in FIGS. 4A–B, or a single spring contained within the transpalatal member 16 as shown in FIG. 7. It should be understood, however, as discussed above, that the stress breaker is not limited to the biasing elements as disclosed herein and can be any mechanical or elastomeric device which imparts a constant force so as to allow the transpalatal member to perform its finctions as disclosed herein. In the present embodiment, the torsional springs 48 that comprise the biasing elements 46 and 47 have a substantially M-shaped construction, each having opposed ends 50 and 52 that extend substantially parallel to the intermediate portion 32 of the transpalatal member 16 and each connect to one of the transverse end portions 42 and 44 of the center connector 38 of the stress breaker, and further include an indention or notch 54 formed approximately in the center of the torsional spring and adapted to be received and fit within the recesses of the caps for the implants as illustrated in FIG. 3.

The stress breaker 18 performs the function of enabling the transpalatal member attached to a tooth or teeth of the patient to maintain such teeth in rigid alignment relative to the anchor of the orthodontic anchor system. The stress breaker further enables the transpalatal member to flex vis-à-vis the anchor(s) when occlusive or other forces are applied to the teeth such as during chewing to reduce the load applied to the implants. Thus, the biasing force exerted by the stress breaker tends to maintain the transpalatal member in its desired position as secured to the anchors until such biasing forces are overcome by the forces of occlusion, in which case the biasing elements will enable the transpalatal member to flex and move to absorb the shock of the biting or occlusive forces and thereafter will return the transpalatal member to its desired position. As result, the implants used for the anchor mechanism can be significantly reduced in size to make the implants as unobtrusive and noninvasive as possible without sacrificing the integrity of the anchors to hold the transpalatal member in place. In turn, this enables the time, expense, and trauma to the patient in installing the implants to be significantly reduced as the reduced size implants can be quickly and easily installed and removed in the palate of a patient's mouth during an in-office visit procedure instead of requiring major surgery.

FIG. 4 illustrates an alternate embodiment of the orthodontic anchor system 55 using a plurality of dental implants 56 and 57 which are one-piece dental implants, each including a shank 58 for insertion into the palate and a head portion 60 having a recess 72 formed into its upper portion for receiving and attaching a stress breaker 64 thereto. Dental implants 56 and 57 further include a recess or opening 66 formed in the top surface of their head portions 60 to enable the attachment of a hexagonal wrench or other driving means for inserting the implant into the palate. The stress breaker 60 of this embodiment includes a series of biasing elements here shown as coil springs 68 which are attached at one end 69 to a connecting member 70 such as a ring or band or similar device that fits within the recesses 62 of the implants 56 and 57, and attach at their opposite ends 71 to a connector 72. As shown in FIG. 4, the connector 72 generally is a cylindrical sleeve or tube formed from metal, plastic or other noncorrosive material through which a transpalatal member 74 is received and attached to the stress breaker and thus the anchors. The transpalatal member is supported by the stress breaker and anchors and is attached at its ends to selected ones of the patient's teeth as discussed above. In use, the implants 56 and 57 are secured at selected locations within the palate. Thereafter, the transpalatal member is attached to the selected teeth and secured to the anchors/implants by the attachment of the stress breaker to the implants. The connecting members 70 of the stress breaker 64 are placed over the top of the implants and fit within the recesses 62 of the implants to secure the transpalatal member 16 thereto.

FIG. 4B illustrates an alternate embodiment of the orthodontic anchor system similar to that shown in FIG. 4A, in which the anchor mechanism comprises dental implants 76 and 77. Each implant 76 and 77 includes a lower threaded portion or shank 78 and a head portion 80 over which is received an upper cap 82. A series of springs 84, here shown as coil springs, attach to the caps and to a connector sleeve 86. As shown in FIG. 4B, the lower portions of implants 76 and 77 are shown as embedded into the bone B of the palate P. The head portions 80 of the implants include a square extension 88 upon which its cap 82 is received. The caps each preferably further include a wire 90 to which one end of each pair of springs is attached, while the opposite ends of the springs are secured to the connector 86.

The connector is a sleeve or tube, formed from a metal, plastic or other noncorrosive material, and received a transpalatal member 92 therethrough. It should be noted that the insertion of the ligature wire into the cap and through the square extensions of the dental implants effectively secures the transpalatal member in place, once the anchors are adequately affixed within the palate.

Figure 5:
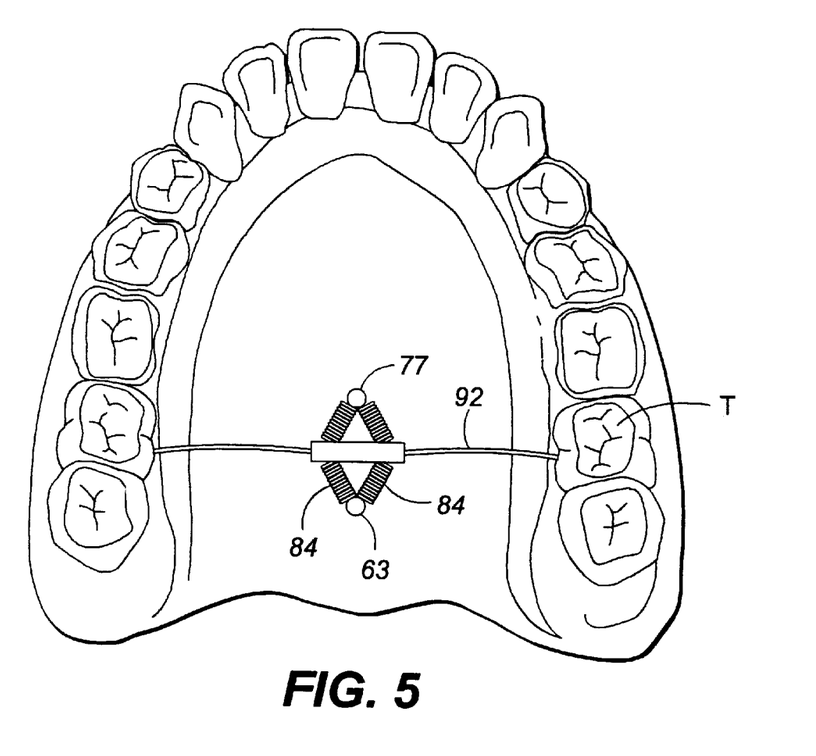
FIG. 5 is a bottom view of the embodiment of the orthodontic anchor system of FIGS. 4A–4B affixed to the palate within the mouth of a patient.

As shown in FIG. 5, the orthodontic anchor systems as shown in FIGS. 4A and 4B are affixed within the mouth of a patient so as to be roughly centered on the palate P of the patient. the transpalatal member is attached at each end to selected teeth and is held centered between the implants by the plurality of springs which provide the biasing stress breaking functions as previously described.

Figure 6:
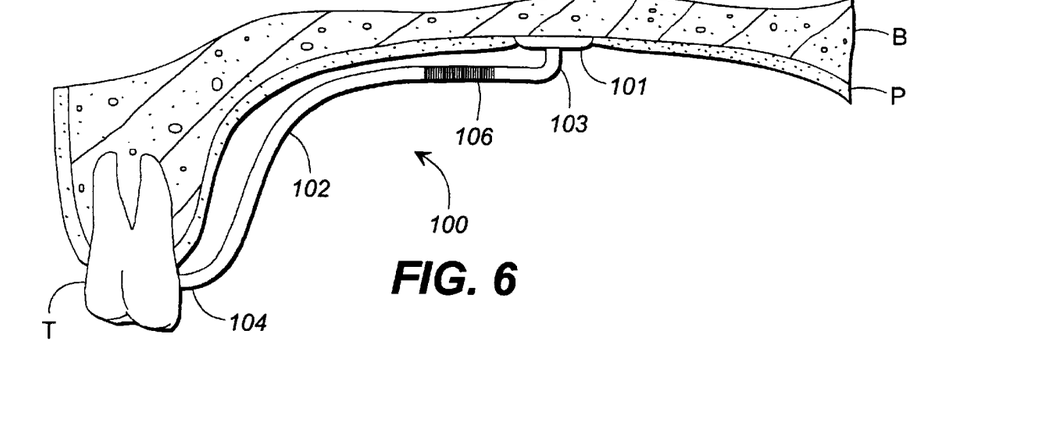
FIG. 6 is a side elevational view, taken in partial cross section, of a further alternate embodiment of the orthodontic anchor system illustrating the anchor as a subperiosteal implant, with a transpalatal member attached at one end to the implant and at the other end to a tooth, with a stress breaker therebetween.

FIGS. 6 and 7 illustrate another alternate embodiment of the orthodontic anchor system 100 wherein the anchor mechanism is a subperiosteal implant 101, called an "on-plant," to which a transpalatal member 102 is attached at a first end 103 and at its other second end 104 to a tooth T. The subperiosteal implant is generally of a type known in the art, such as is taught in U.S. Pat. No, 5,066,224 and U.S. Pat. No. 5,538,427. An advantage of the subperiosteal implant is that it is not inserted deeply within the palate, but rather is adhered to the bone B of the palate P by a hydroxylapetite or similar means to provide adequate anchoring to the transpalatal member. As shown in FIG. 6, a stress breaker 106 is mounted along an intermediate portion of the transpalatal member, formed as a part of the transpalatal member to provide the transpalatal member with the ability to flex and absorb the shock from the forces of occlusion.

Figure 8:
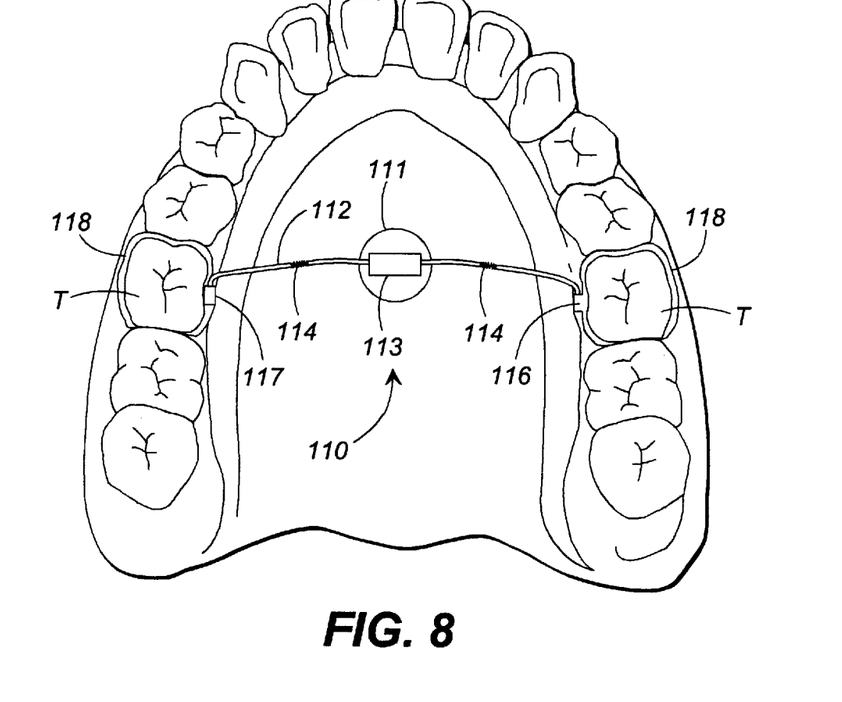
FIG. 8 is a bottom view of another embodiment of the orthodontic anchor system, similar to FIGS. 6–7, illustrating the anchor as a subperiosteal implant, with a transpalatal member attached at an intermediate portion to the anchor, and including a plurality of stress breakers.

FIG. 8 illustrates still another embodiment of the orthodontic anchor system 110 wherein the anchor mechanism is a subperiosteal implant 111 attached to the palate of a patient, but with a transpalatal member 112 is attached thereto at a center portion 113 extending across the patient's mouth. The transpalatal member includes a plurality of stress breakers 114, formed as springs or similar biasing or shock absorbing elements, on each side of the subperiosteal implant, and the transpalatal member is attached at a first end 116 and a second end 117 each to a sleeve 118 encircled about a selected tooth T The plurality of stress breakers allow the transpalatal member to absorb and withstand occlusive or other forces generated from its attached teeth during mastication without imparting such forces to the subperiosteal implant to dislodge it from the palate.

Figure 9:
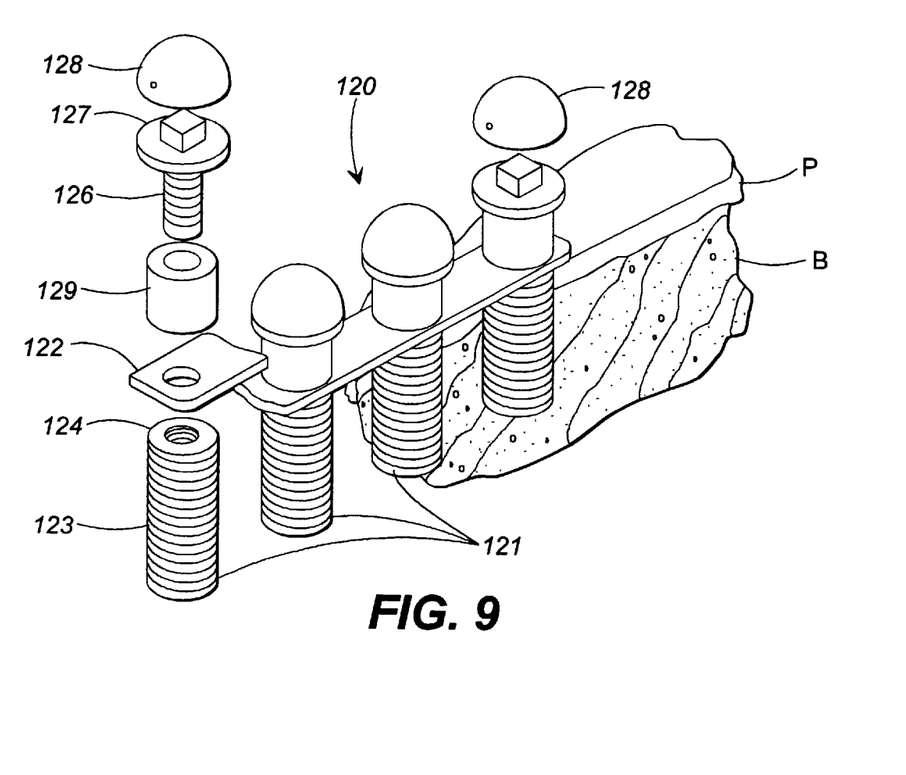
FIG. 9 is a perspective view of a plurality of dental implants which alternatively can comprise the anchor of the orthodontic anchor system.

FIG. 9 illustrates an additional embodiment of the anchor 120 for the present inventive orthodontic anchor system, which includes a series of implants 121 attached by a connector such as a bar or strap 122. Each implant 121 generally is formed from a metal or alloy material and includes a lower threaded portion 123, which has an internally threaded bore 124, and an upper threaded portion 126 having a square extension or projection 127 over which a cap 128 which fits thereto. Further, a sleeve 129 may be inserted between the lower portion and upper portion such that the height of the cap 128 can be adjusted relative to the surface of the palate.

Such an anchor 120 is preferably used when a tremendous amount of force is to be dissipated and/or withstood by the present inventive orthodontic anchor system. Either the springs or semimetallic biasing elements can be used as the stress breaker in the present inventive system between two or more of the plurality of implants 121. Moreover, the use of the anchor 120 allows a transpalatal member and the stress breaker to be selectively positioned within the length of the anchor to rest at an optimal distance to teeth desired to be controlled.

While there has been shown a preferred and alternate embodiments for the present invention, it is to be understood that the invention may be embodied otherwise than is herein specifically shown and described, and that within the embodiments, certain changes may be made in the form, arrangements, and material of the parts without departing from the underlying ideas or principles of this invention as set forth in the claims appended herewith.

What is claimed is:

1. An orthodontic anchor system for supporting an orthodontic appliance on the palate of a patient, comprising:

an anchor adapted to be mounted to the palate of the patient; and a transpalatal member supported by said anchor and having at least one end for attaching at least one tooth of the patient, said member applying an adjusting force to at least one tooth of the patient; and a stress breaker positioned along said transpalatal member to enable said transpalatal member to withstand forces of occlusion without dislodging said anchor from the palate of the patient.

2. The orthodontic anchor system of claim 1, wherein said anchor comprises at least one dental implant.

3. The orthodontic anchor system of claim 1, wherein said anchor comprises at least one subperiosteal implant.

4. The orthodontic anchor system of claim 1, wherein said stress breaker includes a biasing element.

5. The orthodontic anchor system of claim 1, wherein said transpalatal member comprises an elongate bar formed from a material from the group of stainless steel, nickel titanium alloy, titanium molybdenum alloy, superelastic alloy, ceramic and plastic materials.

6. The orthodontic anchor system of claim 1, and further including a band for being received about the tooth of the patient and to which said transpalatal member is attached to secure said transpalatal member to the tooth.

7. The orthodontic anchor system of claim 1 and wherein said stress breaker comprises a connector in which said transpalatal member is received and a series of springs attached to said anchor and to said connector for attaching said transpalatal member to said anchor while enabling said transpalatal member to flex and withstand forces of occlusion applied thereto without dislodging said anchor to enable said anchor to be of a reduced size.

8. The orthodontic anchor system of claim 1 and wherein said stress breaker comprises a biasing element formed along said transpalatal member as an integral part thereof.

9. The orthodontic anchor system of claim 1 and wherein said transpalatal member includes a first end attached to said anchor, a second end attached to the tooth of the patient and an intermediate portion along which said stress breaker is formed as a part thereof.

10. An orthodontic anchor system, comprising:
    an anchor adapted to be mounted within the patient's mouth;
    a transpalatal member having a first end, a second end, and a center portion, said first end and said second end each respectively selected for attaching to at least one tooth for applying an adjusting force thereto; and
    a stress breakers mounted to said anchor and to said transpalatal member and including biasing elements for attaching said transpalatal member to said anchor with a semi-rigid attachment to enable said transpalatal member to flex in response to forces of occlusion.

11. The system of claim 10, wherein said anchor comprises a series of dental implants.

12. The system of claim 10, wherein said anchor comprises at least one subperiosteal implant.

13. The system of claim 10, wherein each said biasing element comprises a spring.

14. The system of claim 10, wherein said dental implants are of a reduced size of less than approximately 21 mm in length.

15. The orthodontic anchor system of claim 10, wherein said transpalatal member comprises an elongate bar formed from a material from the group of stainless steel, nickel titanium alloy, titanium molybdenum alloy, superelastic alloy, ceramic and plastic materials.

16. The system of claim 10, and wherein said anchor includes a plurality of subperiosteal implants.

17. An orthodontic anchor system, comprising:
    a plurality of anchors for selective attachment to a palate;
    a transpalatal member having a first end, a second end, and a center portion, each said first end and second end respectively selected for attaching to at least one tooth; and
    a stress breaker attached to said plurality of anchors and receiving said center portion of said transpalatal member therein, whereby said stress breaker semi-rigidly holds said transpalatal member to said plurality of anchors.

18. The system of claim 17, wherein said anchors comprise dental implants each having a shank adapted to be inserted into the palate and a head portion exposed from the palate.

19. The system of claim 17, wherein said anchors comprise subperiosteal implants adapted to be applied to the palate of a patient.

20. The system of claim 17, wherein said stress breaker includes of at least one semi-rigid biasing element and a connector for receiving said center portion of said transpalatal member to attach and support said transpalatal member between said anchors.

21. The system of claim 20, wherein said biasing element comprises a torsion spring.

22. The system of claim 20, and wherein said biasing element comprises a coil spring.

* * * * *